(12) United States Patent
Gross

(10) Patent No.: US 7,947,736 B2
(45) Date of Patent: May 24, 2011

(54) OLIGOMERIC COMPOUNDS

(75) Inventor: Richard A. Gross, Brooklyn, NY (US)

(73) Assignee: BTG International Limited, London (GB)

( * ) Notice: Subject to any disclaimer, the term of this patent is extended or adjusted under 35 U.S.C. 154(b) by 903 days.

(21) Appl. No.: 11/632,638

(22) PCT Filed: Jul. 15, 2005

(86) PCT No.: PCT/US2005/025308
§ 371 (c)(1),
(2), (4) Date: Mar. 2, 2007

(87) PCT Pub. No.: WO2006/020137
PCT Pub. Date: Feb. 23, 2006

(65) Prior Publication Data
US 2007/0208081 A1    Sep. 6, 2007

Related U.S. Application Data

(60) Provisional application No. 60/588,316, filed on Jul. 16, 2004.

(51) Int. Cl.
*A61K 31/225* (2006.01)
*A61K 47/00* (2006.01)
*C07C 69/66* (2006.01)

(52) U.S. Cl. .................. 514/547; 560/185; 424/439

(58) Field of Classification Search .......... 514/547; 435/135; 560/185; 424/439
See application file for complete search history.

(56) References Cited

U.S. PATENT DOCUMENTS

| | | |
|---|---|---|
| 3,284,298 A | 11/1966 | Hajime et al. |
| 4,067,999 A | 1/1978 | Glabe et al. |
| 4,211,846 A | 7/1980 | Lafferty |
| 4,234,599 A | 11/1980 | Van Scott et al. |
| 4,346,107 A | 8/1982 | Cavazza et al. |
| 4,351,835 A | 9/1982 | Stanko |
| 4,363,815 A | 12/1982 | Yu et al. |
| 4,579,955 A | 4/1986 | Lammerant et al. |
| 4,701,443 A | 10/1987 | Nelson et al. |
| 4,771,074 A | 9/1988 | Lammerant et al. |
| 4,929,449 A | 5/1990 | Veech |
| 4,970,143 A | 11/1990 | Guidoux et al. |
| 4,983,766 A | 1/1991 | Imwinkelried et al. |
| 4,997,976 A | 3/1991 | Brunengraber et al. |

(Continued)

FOREIGN PATENT DOCUMENTS

WO    WO 2004/077938 A2    9/2004

OTHER PUBLICATIONS

International Preliminary Report on Patentability; International Application No. PCT/US2005/026000, (6 pgs), International Filing date Jul. 22, 2005.

(Continued)

*Primary Examiner* — Taylor Victor Oh
(74) *Attorney, Agent, or Firm* — Nixon & Vanderhye

(57) ABSTRACT

Method for the synthesis of a compound of formula H(OCH[CH$_3$]CH$_2$C[O])$_3$—O-A-O—R wherein A is the residue of 1,3-butandiol and R is H or H(OCH[CH$_3$]CH$_2$C[O]$_3$—. The method comprises reacting a cyclic oligomer of (R)-3-hydroxybutyrate consisting of (R)-3-hydroxybutyrate moieties with a 1,3-butandiol in an organic solvent in the presence of *Candida antarctica* lipase type B in a furan or pyran solvent.

15 Claims, 8 Drawing Sheets

Scheme I. Synthesis of (R,R,R)-4,8,12-trimethyl-1,5,9-trioxadodeca-2,6,10-trione ([R]-3HB-triolide)

U.S. PATENT DOCUMENTS

| | | | |
|---|---|---|---|
| 5,100,677 | A | 3/1992 | Veech |
| 5,116,868 | A | 5/1992 | Chen et al. |
| 5,126,373 | A | 6/1992 | Brunengraber et al. |
| 5,200,200 | A | 4/1993 | Veech |
| 5,286,842 | A | 2/1994 | Kimura ............ 528/353 |
| 5,292,774 | A | 3/1994 | Hiraide et al. |
| 5,348,979 | A | 9/1994 | Nissen et al. |
| 5,654,266 | A | 8/1997 | Chen et al. |
| 5,693,850 | A | 12/1997 | Birkhahn et al. |
| 5,719,119 | A | 2/1998 | Veech |
| 5,912,269 | A | 6/1999 | Tung |
| 6,136,862 | A | 10/2000 | Hiraide et al. |
| 6,207,217 | B1 | 3/2001 | Peoples et al. ............ 426/635 |
| 6,207,856 | B1 | 3/2001 | Veech |
| 6,323,237 | B1 | 11/2001 | Veech |
| 6,380,244 | B2 | 4/2002 | Martin et al. |
| 6,384,252 | B1 | 5/2002 | Pageat |
| 6,835,750 | B1 | 12/2004 | Henderson |
| 6,924,129 | B2 * | 8/2005 | Gross et al. ............ 435/100 |
| 2002/0132846 | A1 | 9/2002 | Stone |
| 2004/0266872 | A1 | 12/2004 | Veech |
| 2006/0280721 | A1 | 12/2006 | Veech et al. |
| 2007/0225252 | A1 * | 9/2007 | Gross ............ 514/54 |

OTHER PUBLICATIONS

International Preliminary Report on Patentability, International Application No. PCT/US2005/025369; International Filing Date Jul. 19, 2005 (5 pgs).

International Search Report of PCT/US05/25308, mailed Jul. 21, 2006.

Gross, R.A., et al; "Polymer Synthesis by In Vitro Enzyme Catalysis"; *Chem. Rev.*, vol. 101; pp. 2097-2124 (2001).

Gross, R.A., et al; "Polyester and polycarbonate synthesis by in vitro enzyme catalysis"; *Appl. Microbial Biotechnol.*, vol. 55; pp. 655-660 (2001).

Chen, B., et al; "*Candida antarctica* Lipase B Chemically Immobilized on Epoxy-Activated Micro- and Nanobeads: Catalysis for Polyester Synthesis"; *Biomacromolecules*, vol. 9; pp. 463-471 (2008).

Kumar, A., et al; "*Candida antartica* Lipase B Catalyzed Polycaprolactone Synthesis: Effects of Organic Media and Temperature"; *Biomacromolecules*, vol. 1; pp. 133-138 (2000).

Mahapatro, A., et al; "Lipase-Catalyzed Polycondensations: Effect of Substrates and Solvent on Chain formation, dispersity, and End-Group Structure"; *Biomacromolecules*; vol. 4, pp. 544-551 (2003).

Mahapatro, A., et al; "Mild, Solvent-Free ω-Hydroxy Acid Polycondensations Catalyzed by *Candida antarctica* Lipase B"; *Biomacromolecules*; vol. 5; pp. 62-68 (2004).

Kumar, A., et al; "*Candida antarctica* Lipase B-Catalyzed Transesterification: New Synthetic Routes to Copolyesters"; *J. Am. Chem. Soc.*, vol. 122; pp. 11767-11770 (2000).

Kumar, R., et al; "Biocatalytic Route to Well-Defined Macromers Built around a Sugar Core"; *J. Am. Chem. Soc.*, vol. 124, No. 9; pp. 1850-1851 (2002).

MacDonald, R.T., et al; "Enzyme-Catalyzed ε-Caprolactone Ring-Opening Polymerization"; *Macromolecules*; vol. 28; pp. 73-78 (1995).

Svirkin, Y.Y., et al; "Enzyme-Catalyzed Stereoelective Ring-Opening Polymerization of α-Methyl-β-propiolactone"; *Macromolecules*; vol. 29; pp. 4591-4597 (1996).

Shi, F., et al; "Fractionation and Characterization of Microbial Polyesters Containing 3-Hydroxybutyrate and 4-Hydroxybutyrate Repeat Units"; *Macromolecules*; vol. 30; pp. 2521-2523 (1997).

Fu, H., et al; "Physical Characterization of Sorbitol or Glycerol Containing Aliphatic Copolyesters Synthesized by Lipase-Catalyzed Polymerization"; *Macromolecules*, vol. 36; pp. 9804-9808 (2003).

Mei, Y., et al; "Kinetics and Mechanism of *Candida antarctica* Lipase B Catalyzed Solution Polymerization of ε-Caprolactone"; *Macromolecules*, vol. 36; pp. 5530-5536 (2003).

Mahapatro, A., et al; "Solvent-Free Adipic Acid/1,8-Octanediol Condensation Polymerizations Catalyzed by *Candida antartica* Lipase B"; *Macromolecules*, vol. 37; pp. 35-40 (2004).

Loeker, F.C., et al; "Enzyme-Catalyzed Ring-Opening Polymerization of ε-Caprolactone in Supercritical Carbon Dioxide"; *Macromolecules*, vol. 37; pp. 2450-2453 (2004).

van As, B.A.C., et al; "One-Pot Chemoenzymatic Cascade Polymerization under Kinetic Resolution Conditions"; *Macromolecules*, vol. 37; pp. 8973-8977 (2004).

Kulshrestha, A.S., et al; "Lipase Catalysis. A Direct Route to Linear Aliphatic Copolyesters of Bis(hydroxymethyl)butyric Acid with Pendant Carboxylic Acid Groups"; *Macromolecules*, vol. 38; pp. 3205-3213 (2005).

Hu, S., et al; "Selective enzymatic epoxidation of dienes: generation of functional enantiomerically enriched diene monoepoxy monomers"; *Tetrahedron Letters*; vol. 43; pp. 6763-6766 (2002).

Tewari, Y.B., et al; "Thermodynamics of the lipase-catalyzed esterification of glycerol and *n*-octanoic acid in organic solvents and in the neat reaction mixture"; *Journal of Molecular Catalysis B: Enzymatic*; vol. 15; pp. 135-145 (2001).

Bisht, K.S., et al; "Enzyme-Catalyzed Ring-Opening Polymerization of ω-Pentadecalactone"; *Macromolecules*; vol. 30; pp. 2705-2711 (1997).

Bisht, K.S., et al; "Lipase-Catalyzed Ring-Opening Polymerization of Trimethylene Carbonate"; *Macromolecules*; vol. 30; pp. 7735-7742 (1997).

Kumar, A., et al; "Copolymerizations of ω-Pentadecalactone and Trimethylene Carbonate by Chemical and Lipase Catalysis"; *Macromolecules*; vol. 34; pp. 3527-3533 (2001).

Mei, Y., et al; "Probing Water-Temperature Relationships for Lipase-Catalyzed Lactone Ring-Opening Polymerizations"; *Macromolecules*; vol. 35; pp. 5444-5448 (2002).

Bankova, M., et al; "Mass-Selective Lipase-Catalyzed Poly(ε-caprolactone) Transesterification Reactions"; *Macromolecules*; vol. 35; pp. 6858-6866 (2002).

Focarete, M.L., et al; Copolymers of ω-Pentadecalactone and Trimethylene Carbonate from Lipase Catalysis: Influence of Microstructure on Solid-State Properties; *Macromolecules*; vol. 35; pp. 8066-8071 (2002).

Kumar, A., et al; "Versatile Route to Polyol Polyesters by Lipase Catalysis"; *Macromolecules*; vol. 36; pp. 8219-8221 (2003).

Nakaoki, T., et al; "*Candida antarctica* lipase B catalyzed polymerization of lactones: Effects of immobilization matrices on polymerization kinetics & molecular weight"; *Industrial Biotechnology*; pp. 126-134 (2005).

Bisht, K.S., et al; "Monomer and Polymer Synthesis by Lipase-Catalyzed Ring-Opening Reactions"; *American Chemical Society*; pp. 90-111 (1998).

Gross, R.A., et al; "Polyester and polycarbonate synthesis by in vitro enzyme catalysis"; *Appl. Microbiol. Biotechnol*; vol. 55; pp. 655-660 (2001).

Focrete, M.L., et al; "Physical Characterization of Poly(ω-pentadecalactone) Synthesized by Lipase-Catalyzed Ring-Opening Polymerization"; *Journal of Polymer Science; Part B: Polymer Physics*; vol. 39; pp. 1721-1729 (2001).

Ceccorulli, G., et al; "Cocrystallization of Random Copolymers of ω-Pentadecalactone and ε-Caprolactone Synthesized by Lipase Catalysis"; *Biomacromolecules*; vol. 6; pp. 902-907 (2005).

* cited by examiner

Scheme I. Synthesis of (R,R,R)-4,8,12-trimethyl-1,5,9-trioxadodeca-2,6,10-trione ([R]-3HB-triolide)

Production of the mono-adduct (KTX 0202)

Production of mono-adduct (KTX 0202) and di- adduct (KTX 0203)

OLIGOMERIC COMPOUNDS

This application is the US national phase of international application PCT/US2005/025308, filed 15 Jul. 2005, which designated the U.S. and claims benefit of U.S. 60/588,316, filed 16 Jul. 2004, the entire contents of each of which are hereby incorporated by reference.

The present invention relates to novel oligomeric compounds that have utility as nutraceuticals and/or as medicaments for producing ketosis in humans and animals for nutraceutical or therapeutic purposes.

BACKGROUND OF THE INVENTION

It is known that ketone bodies, particularly (R)-3-hydroxybutyrate (D-β-hydroxybutyrate) and acetoacetate, have both nutritional and therapeutic applications in man and many species of animals. U.S. Pat. No. 6,136,862 and U.S. Pat. No. 6,232,345 (incorporated herein by reference) relate to the use of D-β-hydroxybutyrate, oligomers, esters and salts thereof, inter alia, in the treatment of cerebral edema and cerebral infarction. U.S. Pat. No. 6,207,856 and PCT/US99/21015 also refer to β-hydroxybutyrate and its oligomers, esters and salts thereof in protecting against other forms of nearodegeneration inter alia, through their proposed ability to activate the tricarboxylic acid (TCA) cycle and, through favourable redox reactions in cells and antioxidant activity, scavenge free radicals. β-Hydroxybutyrate has also been demonstrated to have cardioprotectant effect and can increase cardiac efficiency (Sato et al, FASEB J, 9: 651-658, 1995).

It is also known, based on studies of the EEG power spectra measured in freely-moving rats, that D-β-hydroxybutyrate and the induction of ketosis have therapeutic utility in the treatment of conditions including, but not limited to, affective and related psychiatric disorders, which include depression, anxiety, schizo-affective disorder, obsessive-compulsive disorder, panic disorder, social anxiety disorder, generalized anxiety disorder and post-traumatic stress disorder, impaired cognitive function and pain (Copending PCT/GB2005/01835); also in providing symptomatic relief in the treatment of Parkinson's Disease (PD) and other CNS disorders resulting from dopamine deficiency in the brain and also treating and preventing attention deficit hyperactivity disorder (ADHD) and related CNS disorders of cognition, impulsiveness, attention and aggression in children, adolescents and adults (Copending U.S. Provisional Applications 60/611301 and 60/611302).

U.S. Pat. No. 6,207,856, U.S. Pat. No. 6,136,862, U.S. Pat. No. 6,207,856 and PCT/US99/21015, incorporated herein by reference, teach that preferred ketogenic precursors for producing such ketosis are monohydric-, dihydric and trihydric alcoholic esters of (R)-3-hydroxybutyrate, but particularly a (R)-3-hydroxybutyryl ester of (R)-1,3-butandiol, more preferably the diester formed from two molecules of (R)-3-hydroxybutyrate and one molecule of (R)-1,3-butandiol.

However, it is also known that production of oligomers of (R)-3-hydroxybutyrate in pure form is problematic. PCT/US99/21015 exemplifies a ketogenic oligomer with a mixture of (R)-3-hydroxybutyrate trimer, tetramer and pentamer and exemplifies esters thereof with acetoacetyl trimer, tetramer and pentamer of (R)-3-hydroxybutyrate. Similarly, Hiraide et al (1999) J. Parenteral and Enteral Nutrition Vol 23. No 6 discloses the use of a mixture of dimer and trimer of (R)-3-hydroxybutyrate for studies performed to determine the ability of plasma to degrade these molecules to the monomer, (R)-3-hydroxybutyrate.

In order to ensure that previously untested material is safe and appropriate for human administration, by any route, it is first necessary to evaluate all of its significant components for toxicity and efficacy. In the case of multi-component materials, it is, therefore, necessary to evaluate each one of the components in a variety of toxicology and efficacy tests. Such tasks can be extremely expensive and time-consuming, and inevitably, this will be an important factor in any decision on whether or not to proceed with any particular assessment. Furthermore, a mixture of different components may need to be produced in a set ratio for its safety and efficacy evaluation to be valid.

SUMMARY OF THE INVENTION

The present invention provides various, single component oligomeric ketogenic compounds, which are suitable for use in animals and man for therapeutic and/or nutraceutical purposes.

In a first aspect of the present invention, there is provided a method for the synthesis of a compound of general formula $H(OCH[CH_3]CH_2C[O])_n$—O-A-O—R, wherein n is an integer of 3 to 10, -A- is the residue of a dihydric alcohol and R is H, $C_{1-4}$ alkyl or $H(OCH[CH_3]CH_2C[O])_n$— comprising reacting a cyclic oligomer of (R)-3-hydroxybutyrate containing between 3 and 10 (R)-3-hydroxybutyrate moieties with a dihydric alcohol in an organic solvent in the presence of a lipase.

Preferably the method is for the synthesis of a compound of general formula $H(OCH[CH_3]CH_2C[O])_n$—O-A-O—R, wherein n is an integer of 3 to 5, -A- is the residue of a 1,3 alkyl diol and R is H or $H(OCH[CH_3]CH_2C[O])_n$— comprising reacting a cyclic oligomer of (R)-3-hydroxybutyrate containing between 3 and 5 (R)-3-hydroxybutyrate moieties with a 1,3-alkyl diol in a furan or pyran solvent in the presence of a lipase.

Still more preferably, the method is that wherein n is 3, -A- is a 1,3-butandiol residue, R is H, the cyclic oligomer is (R)-3-hydroxybutyrate triolide, the alcohol is 1,3-butandiol, the solvent is tetrahydrofuran (THF) and the lipase is *Candida antarctica* lipase type B (CAL-B), particularly that available from Novozyme as Novozyme 435.

By the term 'residue of a dihydric alcohol' is intended the moiety remaining after the alcohol is diesterified not including the alcoholic oxygens, thus the residue of 1,3,-butandiol will be the group $CH_3$—(CH—)—$CH_2$—CH2-, with the residue being connected to the rest of the molecule at directly through its 1 and 3 carbons.

Preferably the method is that wherein the 1,3-butandiol is racemic and in one preferred form of that method the product provided is at least 95% mono-adduct wherein R is H.

A further preferred method is that wherein n is 3, A is a 1,3-butandiol residue, R is $H(OCH[CH_3]CH_2C[O])_3$—, the cyclic oligomer is (R)-3-hydroxybutyrate triolide, the alcohol is 1,3-butandiol, the solvent is tetrahydrofuran and the lipase is CAL-B, particularly that wherein the alcohol is (R)-1,3-butandiol. Again, the method is preferably that wherein the enzyme is Novozyme 435.

Still more preferably n is 3, A is a 1,3-butandiol residue, R is $H(OCH[CH_3]CH_2C[O])_3$—, the cyclic oligomer is (R)-3-hydroxybutyrate triolide, the alcohol is (R)-1,3-butandiol, the solvent is a mixture of tetrahydrofuran and toluene in ratio in the range 10:90 to 90:10 and the lipase is CAL-B.

For such method the product is a mixture of mono and di-adducts of $H(OCH[CH_3]CH_2C[O])_3$—, with (R)-1,3-butandiol in ratio of 10:90 to 90:10.

In a convenient embodiment of the invention, the products are separated and purified by column chromatography using a methanol:chloroform mixture. More preferably the mixture is between 1 and 5% methanol and 99 to 95% chloroform v/v.

Cyclic esters of (R)-3-hydroxybutyrate are known in the art and are readily produced by known methods: see for example Seebach et al. Helvetia Chimica Acta Vol 71 (1988) pages 155-167, and Seebach et al. Helvetia Chimica Acta, Vol 77 (1994) pages 2007 to 2033.

In a second aspect, the present invention provides novel esters of (R)-3-hydroxybutyrate having efficacy in raising ketone body levels on administration to humans and animals, particularly, but not exclusively, by the oral, parenteral or intravenous route.

Preferred compounds of the second aspect are compounds of formula I $H(OCH[CH_3]CH_2C[O])_n$—O-A-O—R wherein n is an integer of 3 to 5, A is a residue of an 1,3 alkyl diol and R is H or $H(OCH[CH_3]CH_2C[O])_n$—.

Preferably n is an integer of 3 to 5 and A is the residue of (R)-1,3-butandiol, more preferably (R)-1,3-butandiol.

More preferably n is an integer 3, 4, 5 and A is the residue of (R)-1,3-butandiol.

One particular group of diesters of (R)-1,3-butandiol with said oligomers are those wherein both of the two oligomer components of the ester are identical. Most conveniently the compounds of the second aspect of the present invention are diesters of one equivalent of (R)-1,3-butandiol with two equivalents of the trimer of (R)-3-hydroxybutyrate. These compounds have advantage in that all of the component alcohol and acid moieties are converted to energy producing elements in the body on administration.

In a third aspect of the invention, there is provided a compound of the second aspect of the invention in a substantially pure form, preferably containing no more than 10% by weight, more preferably no more than 5% by weight, of other (R)-3-hydroxybutyrate moiety containing compounds.

Particularly this aspect provides a compound of the second aspect in at in least 90% weight/weight pure form, more preferably at least 95% w/w form. More particularly at least 98% w/w form In a fourth aspect of the invention, there is provided a nutraceutical or pharmaceutical composition comprising a compound of the first aspect together with a foodstuff component or a pharmaceutically acceptable carrier, diluent or excipient. Such foodstuff components may be selected for example from the common food groups such as carbohydrates, proteins, fats and vitamins. Carbohydrates may for example be selected from mono-, oligo- and polysaccharides or may even be alternative mono-, oligo- and polymeric forms of (R)-3-hydroxybutyrate.

In a fifth aspect of the present invention is provided the use of a compound of the first aspect of the present invention for the manufacture of a medicament for producing a physiologically acceptable ketosis. Such medicament will be suitable for treating a number of debilitating conditions that will benefit from the induction of ketosis. These include, but are not limited to, damage to the major organs such as occurring during hemorrhage, myocardial infarction, congestive heart failure, pulmonary infarction, kidney failure, where the medicament may be administered via the appropriate clinical route, which includes, but is not limited to, oral and intravenous.

Where the medicament is intended to be given intravenously, the compounds of the invention may be formulated as solutions. The present compounds have advantage that many of them are water soluble and do not require counterions, such as the sodium, potassium or calcium that is conventional with molecules such as the (R)-3-hydroxybutyrate monomer, acetate or lactate.

Particularly suitable carriers, diluents and excipients which may be utilised for eg. oral and parenteral, formulations, may be selected from conventional options such as those disclosed in the patents listed herein, or in Remington, *The Science and Practice of Pharmacy* 21$^{st}$ Edition, Edit David B Troy ISBN 0-7817-4673-6. for example, see Chapter 39 for Solutions. Emulsions, Suspensions, Syrups, Elixirs and Extracts. For example, Elixirs are clear, optionally flavoured liquids for oral use.

The compounds may also be used for the treatment of neurological and psychiatric conditions, such as stroke, head trauma, neurodegenerative conditions, including Alzheimer's and Parkinson's diseases, epilepsy, pain, spasticity and related motor disorders, affective and related psychiatric disorders, including depression, anxiety, schizo-affective disorder, obsessive-compulsive disorder, panic disorder, social anxiety disorder, generalized anxiety disorder and post-traumatic stress disorder, attention deficit hyperactivity disorder (ADHD) and related CNS disorders of cognition, impulsiveness, attention and aggression, diabetes, and obesity. These compounds can also be used to prevent cytotoxic damage to all end-organ systems, including, but not limited to, the central nervous system including its associated sensory, motor, cognitive and emotional function, heart, lung, liver, kidney and gut, such as occurring during major surgery.

BRIEF DESCRIPTION OF THE DRAWINGS

The present invention will now be described further by reference to the following non-limiting Examples, Schemes and Figures. Further embodiments falling within the scope of the claim will occur to those skilled in the art in the light of these.

FIGURES

Figure 1:
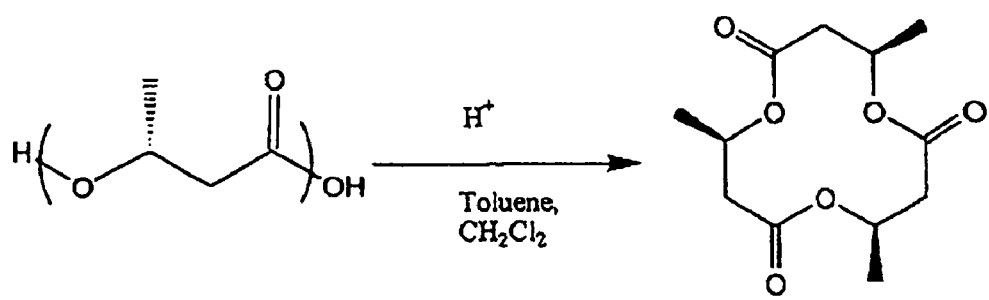

FIG. 1: shows the reaction scheme for synthesis of the triolide of (R)-2-hydroxybutyrate.

Figure 2:
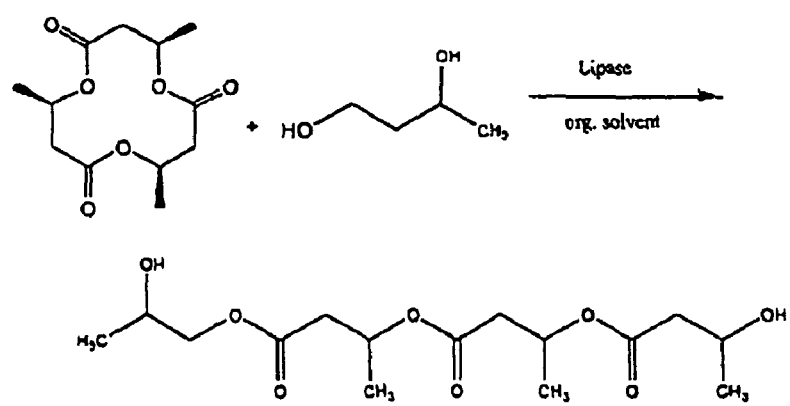

FIG. 2: shows the reaction scheme for synthesis of the mono-adduct (KTX0202).

Figure 3:
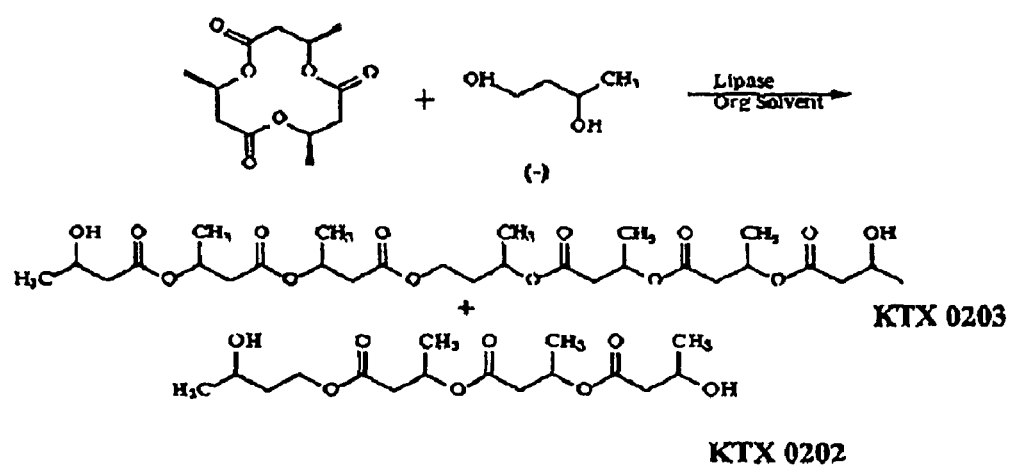

FIG. 3: shows the reaction scheme for synthesis of the mono-adduct and di-adduct KTX0202 and 0203.

Figure 4:
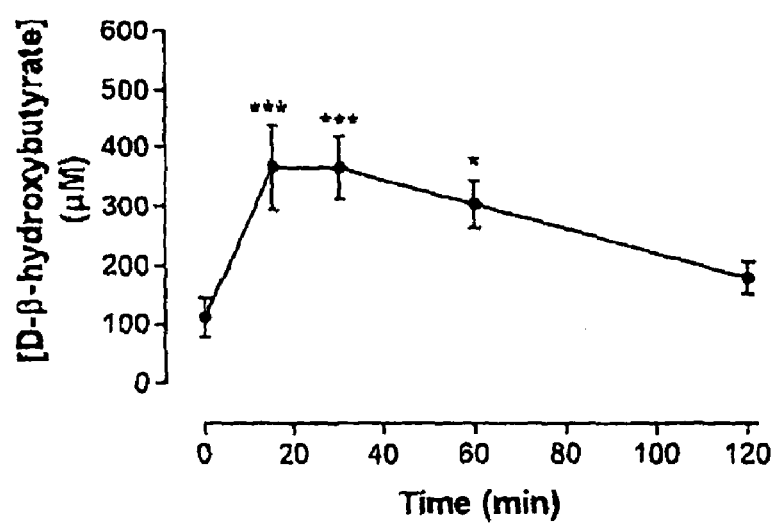

FIG. 4: shows ketogenic effect of oral administration KTX 0101 (sodium β-hydroxybutyrate) as determined by increases of β-hydroxybutyrate concentrations in rat plasma. Animals were dosed with KTX 0101 (300 mg/kg po) and killed at the relevant time-points for collection of plasma. Samples were assayed with the standard Ranbut assay using a 20 µl sample volume and values are shown as mean±SEM, n=4. One-way analysis of variance followed by Dunnett's test was used to compare post-dose time-points to the baseline (T=0) control; ***$P<0.001$, *$P<0.05$.

Figure 5:
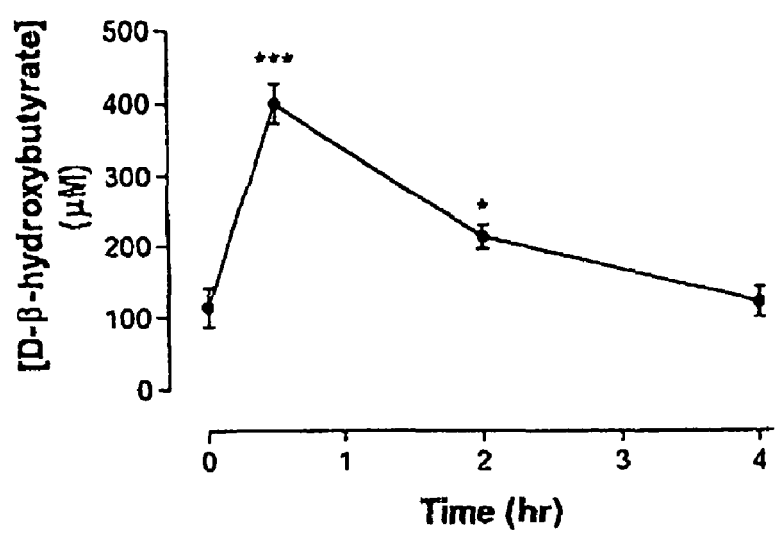

FIG. 5: shows ketogenic effect of oral administration of the mono-adduct (KTX 0202) as determined by increases of β-hydroxybutyrate concentrations in rat plasma. Animals were dosed with KTX 0202 (300 mg/kg po) and groups (n=4) were killed at 30, 120 and 240 minutes for collection of plasma. Terminal cardiac plasma samples were also taken at baseline (T=0). Samples were assayed using the Ranbut β-hydroxybutyrate spectrophotometric assay with a 20 µl sample volume. Values are shown as mean±SEM, n=4. One-way analysis of variance followed by Dunnett's test was used to compare post-dose time-points to the baseline (T=0) control; ***$P<0.001$, *$P<0.05$.

Figure 6:
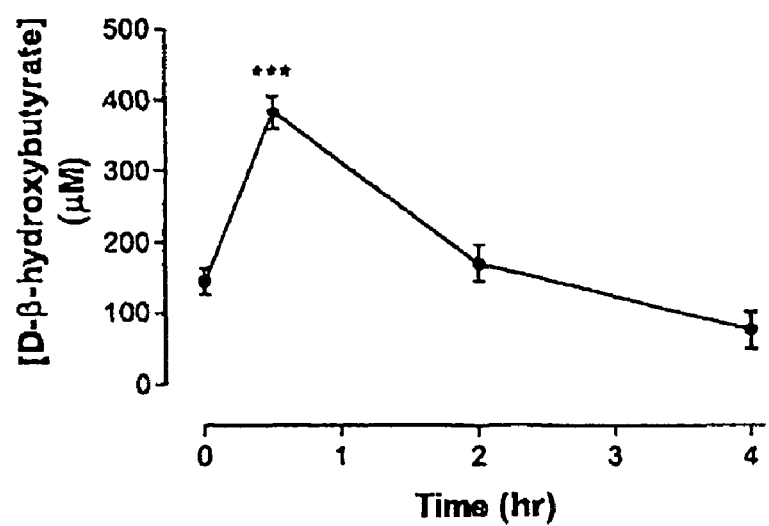

FIG. 6: Ketogenic effect of oral administration of the di-adduct (KTX 0203) as determined by increases of hydroxybutyrate concentrations in rat plasma. Animals were dosed with KTX 0203 (300 mg/kg po) and groups (n=4) were killed at 30, 120 and 240 minutes for collection of plasma. Terminal cardiac plasma samples were also taken at baseline (T=0). Samples were assayed using the Ranbut β-hydroxybutyrate spectrophotometric assay with a 20 μl sample volume. Values are shown as mean±SEM, n=4. One-way analysis of variance followed by Dunnett's test was used to compare post-dose time-points to the baseline (T=0) control; ***P<0.001.

Figure 7:
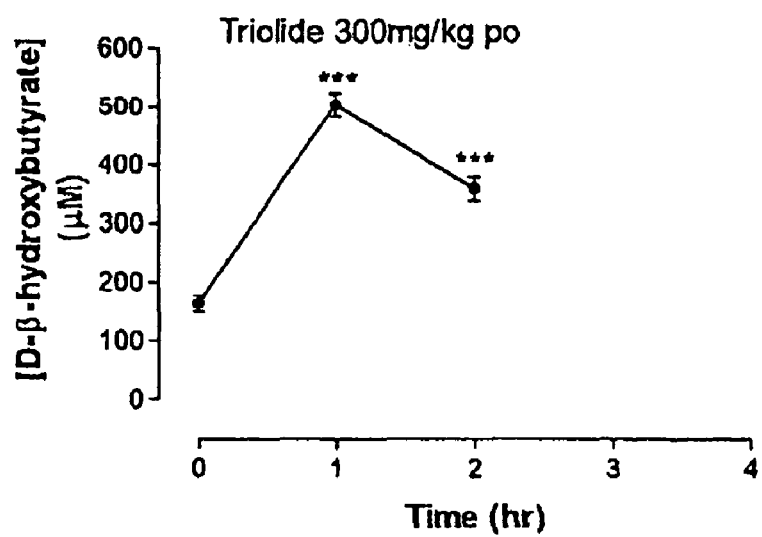

FIG. 7: Shows ketogenic effect of oral administration of the (R)-3-β-hydroxybutyrate triolide as determined by increases of plasma hydroxybutyrate concentrations in rat plasma. Animals were dosed and groups (n=6) killed at the indicated time-points for collection of whole blood and subsequent collection of plasma. Samples were assayed using the Ranbut spectrophotometric assay described (20 μl sample size) and individual values are the mean of triplicate determinations. Group means are shown as ±SEM, n=6. Statistical comparisons against baseline (t=0) were by multiple t-tests (***p<0.001).

Figure 8:
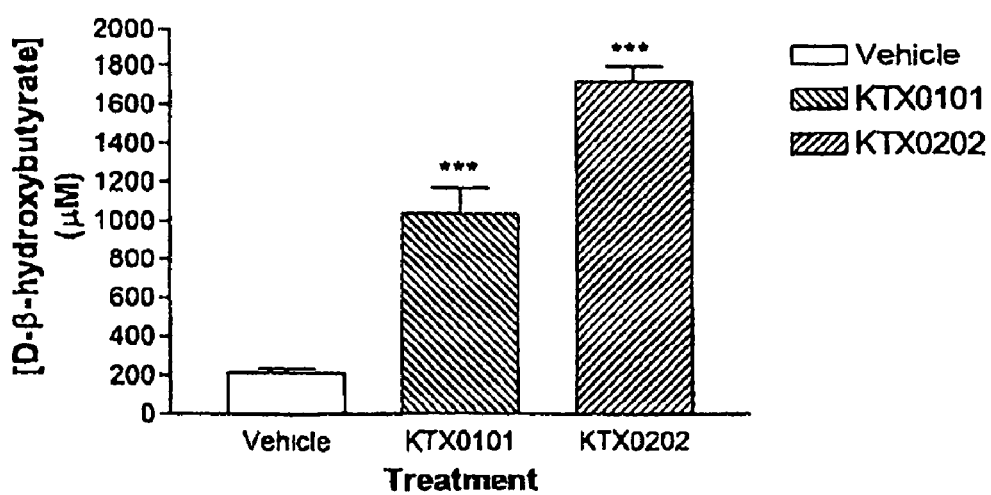

FIG. 8: Shows ketogenic effect of intravenous injection of the mono-adduct (KTX 0202) as determined by increases of plasma hydroxybutyrate concentrations in rat plasma. Animals were dosed with an intravenous bolus and groups (n=6) killed 15 minutes later for the collection of whole blood and subsequent collection of plasma. Samples were assayed with the Ranbut spectrophotometric assays (20 μl sample size) and individual values are the mean of triplicate determinations. Group means are shown as ±SEM, n=6. Statistical comparisons against baseline (t=0) were by multiple t-tests (***p<0.001).

EXAMPLES

General Procedure for the Synthesis of
R-3-hydroxybutyrate triolide from PHB
[poly(3-hydroxybutyrate)] (FIG. 1)

A mixture of poly(3-hydroxybutyrate) (PHB; 36 g) and toluene-4-sulphonic acid monohydrate (23 g) in 750 ml of toluene/dichloroethane (4:1) was heated and stirred at reflux for 20 hrs. The water was removed azeotropically using a Dean-Stark trap for 15 hrs. The resulting clear brown solution was cooled to room temperature, washed with a half-saturated solution of $Na_2CO_3$, then washed with a saturated solution of NaCl, dried over $MgSO_4$, filtered and evaporated to dryness. The crude mixture was purified by column chromatography using silica gel as the stationary phase and a hexane/ethylacetate mixture as the eluent followed by repeated crystallizations. The yield of the purified product was 15 g (40%).

Analysis of the product was as follows: melting point 110° C.; $^1$H NMR (300 MHz, $CDCl_3$): δ 1.30 (9H, d, J=6.4 Hz, $CH_3$), 2.39 (3H, dd, J=2.1, 11.3 Hz), 2.46 (3H, dd, J=11.3, 13.5 Hz) and 5.31-5.39 (3H, m, CH); $^{13}$C NMR (75.5 MHz, $CDCl_3$): δ 20.76 ($CH_3$), 42.16 ($CH_2$), 68.87 (CH) and 170.01 (CO).

Lipase Catalyzed Trans-Esterification Process:

Example 1

Synthesis of 1-(tri(R)-3-hydroxybutyryl-butane-1,3-diol) ester (KTX0202)

The enzyme-catalyzed ring-opening of the (R)-3-hydroxybutyrate triolide (cyclic trimer ester) with racemic 1,3-butandiol was studied as a function of the lipase source, reaction temperature, solvent, and time. The results of this work are given in Table 1.

Into a round-bottom flask (50 ml) was added purified triolide (100 mg, 0.387 mmol), (R,S)-1,3-butandiol (69.8 mg, 0.774 mmol), 1 ml of anhydrous organic solvent, and lipase (34 mg, 20%-by-wt relative to total substrates). The reactions were performed at selected reaction temperatures and times (Table 1). The reactions were terminated by first cooling the reaction mixture to room temperature, removing the enzyme by filtration, and then stripping the solvent by rotary-evaporation. A total of 525 reactions were carried out.

TABLE 1

| Enzyme | Solvent (1) | Temperature (° C.) | Time (hr) | Result |
|---|---|---|---|---|
| Candida cylindrecea lipase (CCL) | 1 to 5 | 1 to 5 | 1 to 3 | Negative |
| Porcine pancreatic lipase (PPL) | 1 to 5 | 1 to 5 | 1 to 3 | Negative |
| Amano pseudomonas cepecia (PS) | 1 to 5 | 1 to 5 | 1 to 3 | Negative |
| Candida antarctica lipase (CAL-B) | 1 to 5 | 1 to 5 | 1 to 3 | Positive in one solvent |
| Mucor meihei | 1 to 5 | 1 to 5 | 1 to 3 | Negative |
| Lipase pseudomonas fluorescence (PF) | 1 to 5 | 1 to 5 | 1 to 3 | Negative |

Solvents: (1) tetrahydrofuran (THF) (2) toluene, (3) acetonitrile, (4) dioxane and (5) diethyl ether. Temperatures: (1) 45, (2) 50, (3) 55, (4) 60 and (4) 70° C. Reaction times: (1) 24, (2) 48, (3) 72 hrs.

CAL-B in THF at 55° C. was the best system for carrying out this reaction. No other lipase was found to be active. The product was purified by column chromatography using silica gel as the stationary phase and $MeOH/CHCl_3$, 2% v/v as the eluent. Analysis of the product was as follows:

Yield: 61% (82 mg) of a transparent oil; IR ($CHCl_3$) $cm^{-1}$: 3447, 2926, 1750, 1392 and 1197; $^1$H NMR (300 MHz, $CDCl_3$): δ 1.20 (12H, d, J=6.4 Hz, $CH_3$), 1.70-1.78 (4H, m, H-3, $COCH_2$), 2.38-2.46 (4H, m, $COCH_2\times2$), 3.11 (1H, brs, OH exchangeable with $D_2O$), 3.88-3.95 (1H, m, CH), 4.16-4.21 (3H, m, $OCH_a,2\times CH$), 4.31-4.38 (1H, m, $CH_b$) and 5.13-5.34 (1H, m, CH); $^{13}$C NMR ($CDCl_3$): δ 20.81, 22.92 ($CH_3$), 38.17 (C-3), 43.68 ($COCH_2\times3$), 62.48 (C-4), 64.66 (C-2), 65.49 (CH) and 173.41 (CO); MS (FAB, 3-NBA) $[M]^+$ (% int): 349.23$[(M+H)^+$, 13], 307.13 (26), 289.11 (18), 263.17 (18), 219.20 (8), 177.13 (48), 154.06 (100) and 137.05 (77).

Thus, this is consistent with the mono-(tri-(R)-3-hydroxybutyrate) adduct, being metabolically equivalent to four units of (R)-3-hydroxybutyrate. In the examples below the mono-adduct is referred to as tetramer, containing three (R)-3-hydroxybutyrate moieties and one butandiol-providing four metabolic equivalents of (R)-3-hydroxybutyrate on metabolism. Similarly the di-adduct is referred to as the heptamer, having six (R)-3-hydroxybutyrate moieties and one butandiol.

Example 2

Synthesis of 1-(tri(R)-3-hydroxybutyryl-butane-1,3-diol (KTX 0202; tetramer) (FIGS. 2 and 3) and of 1-3 butandiol, di-(tri(R)-3-hydroxybutyrate)ester (KTX 0203, heptamer) (FIG. 3)

After successfully completing the ring-opening of triolide using (R,S)-1,3-butandiol, the reaction was repeated as above (CAL-B, in THF, 72 hrs, 55° C.) except that (R)-1,3-butanediol was used in place of its racemate. Thus, into a round-bottom flask (50 ml) was added purified triolide (100 mg, 0.387 mmol), (R)-1,3-butanediol (69.8 mg, 0.774 mmol), 1 ml of an anhydrous organic solvent, and CAL-B (34 mg, 20%-by-wt relative to total substrates). Unexpectedly, in addition to the tetramer that was the primary product using racemic butandiol, the corresponding heptamer was found as a co-product. These two products were separated by column chromatography (MeOH/CHCl$_3$, 2:98 v/v). The structure of tetrameric product was confirmed as follows:

Yield: 42% (56 mg) of a transparent oil; $^1$H NMR (300 MHz, CDCl$_3$): δ 1.20 (12H, 4d, J=6.4 Hz, CH$_3$), 1.70-1.83 (4H, m, H-3, COCH$_2$), 2.41-2.53 (4H, m, COCH$_2$×2), 3.42, 3.69 (2H, brs, OH exchangeable with D$_2$O), 4.19-4.24 (1H, m, CH), 4.29-4.38 (3H, m, OCH$_a$,2×CH), 4.40-4.45 (1H, m, CH$_b$) and 5.12-5.18 (1H, m, CH); $^{13}$C NMR (75 MHz, CDCl$_3$): δ 22.63, 23.55 (CH$_3$), 37.68 (C-3), 43.23 (C-6, C-10, C-14), 62.11 (C-2, C-15), 64.29 (C-7, C-11), 64.89 (C-4) and 172.91 (CO); CHN Analysis: Anal. Calcd for C$_{16}$H$_{28}$O$_8$: C, 55.16; H, 8.10; O, 36.74. Found: C, 54.03; H, 8.85; O, 37.12.

Example 3

Synthesis of 1-(tri(R)-3-hydroxybutyryl-butane-1,3-diol (KTX 0202; tetramer) (FIGS. 2 and 3) and of 1,3 butandiol, di-(tri(R)-3-hydroxybutyrate)ester (KTX 0203; heptamer) (FIG. 3)

The structure of heptamer product was confirmed as follows: Yield: 35% (82 mg) of a transparent oil; $^1$H NMR (300 MHz, CDCl$_3$): δ 1.24-1.30 (21H, m, CH$_3$), 1.87-1.93 (4H, m, H-17, 2×COCH$_2$), 2.38-2.63 (14H, m, COCH$_2$×7), 2.96-3.09 (1H, m, OH), 4.11-4.19 (7H, m, 5×CH, OCH$_2$), and 5.09-5.34 (2H, m, 2×CH); $^{13}$C NMR (7.50 MHz, CDCl$_3$): δ 19.82, 22.61, 23.49 (CH$_3$), 37.80, 38.80, 40.83, 43.44, 62.11 (CH$_2$), 64.40, 64.52, 67.52, 67.88, 68.82 (CH), and 169.59, 170.72, 170.47, 171.88 (CO). CHN Analysis: Anal. Calcd for C$_{28}$H$_{46}$O$_{13}$: C, 56.94; H, 7.85; O, 35.21. Found: C, 54.26; H, 8.28; O, 37.46.

The ratio of the mono to di-adduct produced in the reaction mixture before separation could be altered by solvent changing. Thus by using a 1:1 mixture v:v of THF to toluene, the ratio of mono-di was changed to 2:3, the reaction being monitored using LC:MS. The formation of the heptamer might occur through the triolide ring opening by action of the tetramer. However, it is believed that repetitive transfer of butyrate units from one tetramer to another is the preferred reaction. Early in the reaction only one peak at 371.27 (M+Na) corresponding to the mono adduct was detected followed by transfer of trimer between molecules to give the di-adduct and some (R)-3-hydroxybutyrate monomer, which was subsequently removed in the purification step.

Example 4

Ketogenic Activity After Oral Administration of Esters of the Invention

Male Sprague-Dawley rats (weight range 200-250 g; Clarles River, Margate, Kent) were used. The rats were group-housed in polypropylene cages at a temperature of 21±4° C., 55±20% humidity on a standard 12 hour light/dark cycle (lights on at 6.00 am). Animals had free access to a standard pelleted rat diet and tap water at all times. Animals were acclimatized to these conditions for at least one week before experimentation.

The sodium salt of D-β-hydroxybutyrate monomer (KTX 0101) was used as a comparator for assessing the bioavailability of the oligomeric compounds described here. KTX 0101 (Sigma 298360 Lot 18927HB), KTX 0202 or KTX 0203 were administered by oral gavage (po) at 300 mg/kg. Control animals received the appropriate vehicle (deionized water at 1 ml/kg) via the same route.

| Protocol A: KTX 0101 only | | | |
|---|---|---|---|
| Group | Number of animals | Time of blood sampling (min) | Treatment |
| 3 | 4 | 0 | Vehicle dosed |
| 4 | 4 | 15 | KTX 0101 (sodium D-β-hydroxybutyrate) 300 mg/kg po |
| 5 | 4 | 30 | KTX 0101 300 mg/kg po |
| 6 | 4 | 60 | KTX 0101 300 mg/kg po |

| Protocol B: KTX 0202 and KTX 0203 only | | | |
|---|---|---|---|
| Group | Number of animals | Time of blood sampling (min) | Treatment |
| A | 4 | 0 | Vehicle baseline |
| B | 4 | 30 | KTX 0202 300 mg/kg po or KTX 0203 300 mg/kg po |
| C | 4 | 120 | KTX 0202 300 mg/kg po or KTX 0203 300 mg/kg po |
| D | 4 | 240 | KTS 0202 300 mg/kg po or KTX 0203 300 mg/kg po |

| Protocol E: (R)-3-β-hydroxybutyrate triolide only | | | |
|---|---|---|---|
| Group | Number of animals | Time of blood sampling (min) | Treatment |
| A | 6 | 0 | Vehicle baseline |
| B | 6 | 60 | (R)-3-β-hydroxybutyrate triolide 300 mg/kg po |
| C | 6 | 120 | (R)-3-β-hydroxybutyrate triolide 300 mg/kg po |

In Protocol A, blood (approx 10 ml) was collected by cardiac puncture at 15, 30 and 60 minutes after dosing. In Protocol B, blood (approx 5 ml) was collected by cardiac puncture at 30, 120 and 240 minutes after dosing. In Protocol E, blood (approx 5 ml) was collected by cardiac puncture at 120 and 240 minutes after dosing. Animals were killed by CO$_2$ asphyxiation and blood collected by cardiac puncture. Blood was placed into EDTA-coated plasma collection tubes (Sarstedt 5 ml K2E tubes) and kept on ice prior to centrifugation. Tubes were centrifuged in an Eppendorf 570R centrifuge at 4° C. for 5 minutes at 2500 rpm (1000 g). Plasma samples were initially frozen on dry ice and transferred to a −75° C. freezer until required for analysis.

Commercial clinical assay kits (Ranbut) for the determination of D-β-hydroxybutyrate were obtained from Randox Laboratories (Antrim, UK). The kit quantified NADH via the activity of β-hydroxybutyrate dehydrogenase measured as an increase in OD340 nm. An alkaline pH is necessary to drive the reaction equilibrium towards the production of NADH and acetoacetate.

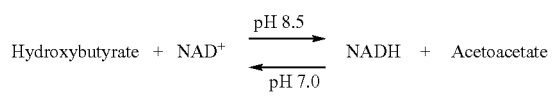

This spectrophotometric assay was modified for application to a 96-well microplate format. The reaction rate was then determined from the increase in OD340 nm over a 1 minute time-course, after allowing a necessary period for the reaction rate to settle.

KTX 0101 (sodium β-hydroxybutyrate); After oral administration at 300 mg/kg, the sodium salt of the monomer rapidly increased plasma concentrations of β-hydroxybutyrate (FIG. 5). The maximum increase was 0.4 mM observed at 15 min (P<0.001), it plateaued 0 at this level until 30 min (P<0.001) and declined thereafter. The level β-hydroxybutyrate was still significantly (P<0.05) elevated at 1 h, but it returned to control values by 2 h.

KTX 0202 (mono-adduct): After oral administration at 300 mg/kg, the tetramer also significantly increased plasma concentrations of β-hydroxybutyrate (FIG. 6). The maximum increase was 0.4 mM observed at 30 min (P<0.001); it declined thereafter, but was still significantly (P<0.05) elevated at 2 h. Plasma β-hydroxybutyrate levels returned to control values by 4 h.

KTX 0203 (di-adduct): After oral administration at 300 mg/kg, the heptamer also significantly increased plasma concentrations of β-hydroxybutyrate (FIG. 7). The maximum increase was 0.4 mM observed at 30 min (P<0.001); it declined thereafter and plasma β-hydroxybutyrate levels returned to control values by 2 h.

(R)-3-β-hydroxybutyrate triolide. After oral administration at 300 mg/kg, the triolide significantly increased plasma concentrations of β-hydroxybutyrate (FIG. 7). The maximum increase was 0.5 mM observed at 60 min (P<0.001); it declined thereafter, but was still significantly (P<0.001) elevated at 2 h.

Example 5

Ketogenic Activity After Intravenous Injection of Esters of the Invention

Male Sprague-Dawley rats (weight range 200-250 g) were obtained from Charles River, Margate, Kent. The rats were group housed in polypropylene cages at a temperature of 21±4° C., a humidity of 55±20% and on a standard light/dark cycle. Animals had free access to a standard pelleted rat diet and tap water at all times. Animals were accustomed to these conditions for at least one week before experimentation.

KTX 0101 (synthesized by KetoCytonyx) was dissolved at 300 mg/ml in deionized water which produced a clear solution of pH 7.0. Similarly, KTX 0202 was dissolved at 300 mg/kg in deionized water and produced a slightly opaque solution with a pH of 6.0. The compounds were infused via the tail vein at 300 mg/kg (1 ml/kg) over a period of 1 to 2 min.

Groups for Each of the Above Compounds:

| Group | Number of animals | Time of blood sampling (min) | Treatment |
| --- | --- | --- | --- |
| A | 6 | 15 | Vehicle |
| B | 6 | 15 | KTX 0101 |
| C | 6 | 15 | KTX 0202 |

Animals were killed 15 min later by $CO_2$ asphyxiation and blood was collected by cardiac puncture. Blood was placed into EDTA-coated plasma collection tubes (Sarstedt 5 ml K2E tubes) and kept on ice prior to centrifugation. Tubes were centrifuged in an Eppendorf 570R centrifuge at 4° C. for 5 minutes at 2500 rpm (100 g). Plasma samples were initially frozen on dry ice and transferred to a −75° C. freezer until required for analysis.

Commercial clinical assay kits (Ranbut) for the determination of D-β-hydroxybutyrate were obtained from Randox Laboratories (Antrim, UK). The kit quantified NADH via the activity of β-hydroxybutyrate dehydrogenase measured as an increase in OD340 nm. An alkaline pH is necessary to drive the reaction equilibrium towards the production of NADH and acetoacetate.

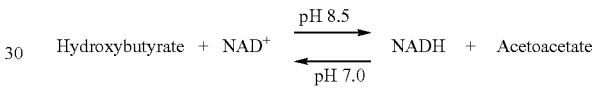

KTX 0101 (sodium β-hydroxybutyrate): After intravenous injection at 300 mg/kg, the sodium salt of the monomer rapidly increased plasma concentrations of β-hydroxybutyrate. An increase to 1.0 mM was recorded at 15 min (P<0.001).

KTX 0202 (mono-adduct): After intravenous injection at 300 mg/kg, the tetramer also rapidly increased plasma concentrations of β-hydroxybutyrate (FIG. 8). An increase to 1.7 mM was recorded at 15 min (P<0.001).

Discussion

These results demonstrate that KTX 0202 (mono-adduct, tetramer of (R)-3-β-hydroxybutyrate) and KTX 0203 (di-adduct, heptamer of β-hydroxybutyrate) are both orally bioavailable and are capable of producing ketosis when given to rats. The magnitude of the increases in plasma β-hydroxybutyrate evoked by KTX 0202 and KTX 0203 are at least as great as those produced by KTX 0101, the sodium salt of β-hydroxybutyrate. Moreover, in the case of KTX 0202, this β-hydroxybutyrate oligomer has an improved biological half-life relative to KTX 0101.

The (R)-3-β-hydroxybutyrate triolide was also able to increase plasma concentrations of β-hydroxybutyrate after being administered via the oral route, as disclosed in WO00/15216. Once again, the elevation of plasma β-hydroxybutyrate was at least as great as that evoked by oral administration of the equivalent dose of KTX 0101. Like KTX 0202, (R)-3-β-hydroxybutyrate triolide has an improved biological half-life relative to KTX 0101.

The results also demonstrate that KTX 0202 (mono-adduct, tetramer of (R)-3-β-hydroxybutyrate) is bioavailable when injected via the intravenous route of administration. When injected at identical doses, ie 300 mg/kg iv, KTX 0202 increased the plasma concentration of β-hydroxybutyrate at 15 min by 60% more than KTX 0101.

Together, these results report a route for the synthesis of the novel oligomers of (R)-β-hydroxybutyrate having advantage of being water soluble and defined for purposes of producing ketosis in subjects. The experimental data also demonstrate that these compounds are biovailable when given by both the oral and intravenous routes of administration. Thus, these compounds will have utility as nutraceuticals, or as medicaments where they can be administered using clinically relevant routes, eg orally or intravenously.

The invention claimed is:

1. A method for the synthesis of a compound of formula

H(OCH[CH₃]CH₂C[O])₃—O-A-O—R wherein
A is the residue of 1,3-butandiol and
R is H or H(OCH[CH₃]CH₂C[O])₃—
comprising reacting a cyclic oligomer of (R)-3-hydroxybutyrate consisting of three (R)-3-hydroxybutyrate moieties with 1,3-butandiol in an organic solvent in the presence of *Candida antarctica* lipase type B in a furan or pyran solvent.

2. A method as claimed in claim 1 wherein the solvent further includes toluene.

3. A method as claimed in claim 1 wherein the cyclic oligomer is (R)-3-hydroxybutyrate triolide and the solvent is tetrahydrofuran.

4. A method as claimed in claim 1 wherein the 1,3-butandiol is racemic and the product is at least 95% mono-adduct with R being H.

5. A method as claimed in claim 1 wherein the alcohol is (R)-1,3-butandiol.

6. A method as claimed in claim 5 wherein the solvent is a mixture of tetrahydrofuran and toluene in ratio in the range 10:90 to 90:10.

7. A method as claimed in claim 6 wherein the product is a mixture of mono and di-adducts of H(OCH[CH₃]CH₂C[O])₃— with (R)-1,3-butandiol in ratio of 10:90 to 90:10.

8. A method as claimed in claim 6 wherein the products are purified by column chromatography using a methanol:chloroform mixture.

9. A method as claimed in claim 8 wherein the mixture is between 1 and 5% methanol and 99 to 95% chloroform v/v.

10. Isolated compound of formula

H(OCH[CH₃]CH₂C[O])₃—O-A-O—R wherein A is a residue of 1,3-butandiol and R is H or H(OCH[CH₃]CH₂C[O])₃—,
free of other compounds containing oligomeric (R)-3-hydroxybutyrate.

11. Isolated compound of formula H(OCH[CH₃]CH₂C[O])₃—O-A-O—R wherein A is —CH₂(CH₃)CHCH₂— of the (R)-optical form,
free of other compounds containing oligomeric (R)-3-hydroxybutyrate.

12. 1-(tri(R)-3-hydroxybutyryl-butane-1,3-diol) in at least 95% weight/weight pure form.

13. 1,3-butandiol, di-(tri(R)-3-hydroxybutyryate) at least 95% weight/weight pure form.

14. A nutraceutical or pharmaceutical composition comprising a compound produced by a method as claimed in claim 1.

15. A nutraceutical or pharmaceutical composition comprising a compound as claimed in claim 10.

* * * * *